United States Patent
Lindstrom et al.

(10) Patent No.: US 12,310,981 B2
(45) Date of Patent: *May 27, 2025

(54) USE OF CHONDROITIN SULFATE FOR RELIEVING OCULAR PAIN

(71) Applicant: SURFACE OPHTHALMICS, INC., Pleasanton, CA (US)

(72) Inventors: Richard L. Lindstrom, Wayzata, MN (US); Kamran Hosseini, Pleasanton, CA (US); Lyle Bowman, Pleasanton, CA (US)

(73) Assignee: SURFACE OPHTHALMICS, INC., Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/555,982

(22) PCT Filed: May 1, 2022

(86) PCT No.: PCT/US2022/027177
§ 371 (c)(1),
(2) Date: Oct. 18, 2023

(87) PCT Pub. No.: WO2022/240598
PCT Pub. Date: Nov. 17, 2022

(65) Prior Publication Data
US 2024/0207305 A1   Jun. 27, 2024

Related U.S. Application Data

(60) Provisional application No. 63/186,747, filed on May 10, 2021.

(51) Int. Cl.
*A61K 31/737* (2006.01)
*A61K 9/00* (2006.01)

(52) U.S. Cl.
CPC .......... *A61K 31/737* (2013.01); *A61K 9/0048* (2013.01)

(58) Field of Classification Search
None
See application file for complete search history.

(56) References Cited

U.S. PATENT DOCUMENTS

| | | | |
|---|---|---|---|
| 4,486,416 A * | 12/1984 | Soll | A61K 31/737 514/54 |
| 5,514,686 A | 5/1996 | Mochizuki et al. | |
| 5,518,732 A | 5/1996 | Nigam | |
| 6,051,560 A * | 4/2000 | Chang | A61K 31/715 536/55.1 |
| 6,489,335 B2 | 2/2002 | Peyman | |
| 6,579,901 B2 | 6/2003 | Chen et al. | |
| 6,878,694 B2 | 4/2005 | Doshi et al. | |
| 7,083,803 B2 | 8/2006 | Peyman | |
| 7,087,237 B2 | 8/2006 | Peyman | |
| 7,335,682 B2 | 2/2008 | Chen et al. | |
| 7,820,639 B2 | 10/2010 | Lindstrom | |
| 8,551,974 B1 | 10/2013 | Lindstrom | |
| 8,574,562 B2 | 11/2013 | Goebel | |
| 8,663,716 B2 * | 3/2014 | Wada | A23L 2/52 424/725 |
| 9,034,843 B2 | 5/2015 | Matsumura et al. | |
| 9,233,123 B1 | 1/2016 | Lindstrom | |
| 9,549,966 B2 | 1/2017 | Hamrah et al. | |
| 9,572,800 B2 | 2/2017 | Zarnitsyn et al. | |
| 9,782,385 B2 * | 10/2017 | Lin | A61K 9/0048 |
| 9,789,080 B2 | 10/2017 | Hou et al. | |
| 10,058,616 B2 | 8/2018 | Hong et al. | |
| 10,201,548 B2 | 2/2019 | Bowman et al. | |
| 10,206,944 B2 | 2/2019 | De Rosa et al. | |
| 10,420,796 B2 | 9/2019 | Funayama et al. | |
| 10,507,230 B2 | 12/2019 | Yamamoto et al. | |
| 10,555,947 B2 | 2/2020 | Musunuri et al. | |
| 10,588,913 B2 | 3/2020 | Tada et al. | |
| 10,716,804 B2 | 7/2020 | Funayama | |
| 11,207,345 B2 | 12/2021 | Funayama et al. | |
| 11,766,421 B2 | 9/2023 | Saadeh et al. | |
| 2001/0041671 A1 | 11/2001 | Napoli | |
| 2003/0130301 A1 | 7/2003 | Ueno | |
| 2005/0063996 A1 | 3/2005 | Peyman | |
| 2006/0110459 A1 | 5/2006 | Jafari et al. | |
| 2006/0148686 A1 | 7/2006 | Xia et al. | |
| 2007/0082841 A1 | 4/2007 | Higuchi et al. | |

(Continued)

FOREIGN PATENT DOCUMENTS

| | | |
|---|---|---|
| CN | 1317342 A | 10/2001 |
| CN | 10299029 A | 6/2011 |

(Continued)

OTHER PUBLICATIONS

Vichyanond et al. "Use of Cyclosporine A and Tacrolimus in Treatment of Vernal Keratoconjunctivitis" Curr Allergy Asthma Rep, (2013) 13:308-314.

Bhatti et al. "Severe acute fibrinous and organzing pneumonia (AFOP) causing ventilatory failure: Successful treatment with mycophenolate mofetil and corticosteroids", Respiratory Medicine (2009) 13:1764-1767.

Dogru et al., "Pharmacotherapy of dry eye", Epert Opin. Pharmacother. (2011)12(3):325-334.

Gipson et al., "Clinical trial of focal segmental glomerulosclerosis in children and young adults", Kidney International (2011) 80:868-878.

Gumus et al., "The role of inflammation and antiinflammation therapies in keratoconjunctivitis sica", Clinical Ophthamology (2009) 3:57-67.

(Continued)

*Primary Examiner* — Dale R Miller
(74) *Attorney, Agent, or Firm* — Raymond Wagenknecht; Biotech Beach Law PC

(57) ABSTRACT

Chondroitin sulfate-based pharmaceutical formulations useful for the treatment of ocular pain or discomfort, such as occurring from ocular surgery, dry eye disease, ocular surgery induced dry eye disease, contact lens induced ocular surface dry eye disease, preservative induced ocular surface disease, conjunctivitis, corneal abrasion, burns, blepharitis, and stye.

10 Claims, 1 Drawing Sheet

(56) References Cited

U.S. PATENT DOCUMENTS

| | | |
|---|---|---|
| 2007/0259021 A1 | 11/2007 | Friedlaender et al. |
| 2007/0280924 A1 | 12/2007 | Daniels et al. |
| 2008/0242646 A1 | 10/2008 | Lessem et al. |
| 2010/0010082 A1 | 1/2010 | Chong et al. |
| 2010/0286065 A1 | 11/2010 | Lambert et al. |
| 2014/0031298 A1 | 1/2014 | Hughes et al. |
| 2017/0161438 A1 | 6/2017 | Connery et al. |
| 2018/0117064 A1 | 5/2018 | Tada et al. |
| 2019/0008920 A1 | 1/2019 | Arumugham et al. |
| 2019/0151338 A1 | 5/2019 | Saadeh |
| 2019/0298738 A1 | 10/2019 | Bowman et al. |
| 2019/0332516 A1 | 10/2019 | Bowman et al. |
| 2020/0129526 A1 | 4/2020 | Tada et al. |
| 2020/0171075 A1 | 6/2020 | Friedman |
| 2022/0071945 A1 | 3/2022 | Hosseini et al. |
| 2022/0143075 A1 | 5/2022 | Saadeh et al. |
| 2023/0277557 A1 | 9/2023 | Sternberg et al. |

FOREIGN PATENT DOCUMENTS

| | | |
|---|---|---|
| EP | 0063973 B1 | 3/1984 |
| EP | 0167363 B1 | 8/1990 |
| EP | 0232377 B1 | 9/1990 |
| EP | 0517972 B1 | 11/1995 |
| EP | 1188434 B1 | 5/2006 |
| EP | 2560616 B1 | 4/2011 |
| EP | 1948131 B3 | 3/2013 |
| EP | 2946782 B1 | 3/2013 |
| EP | 2937088 B1 | 12/2013 |
| EP | 1173177 B2 | 3/2014 |
| EP | 2979689 A1 | 2/2016 |
| EP | 2493942 B1 | 6/2016 |
| EP | 3409292 B1 | 12/2018 |
| EP | 4088757 A1 | 2/2021 |
| EP | 2695621 B1 | 3/2021 |
| EP | 3023108 B1 | 4/2021 |
| EP | 3831394 A1 | 6/2021 |
| JP | 2009-86619 A | 4/2009 |
| JP | 2016050181 A | 4/2016 |
| JP | 2016-188237 A | 11/2016 |
| JP | 2017-206547 A | 11/2017 |
| JP | 2018-83805 A | 5/2018 |
| JP | 2018-203792 A | 12/2018 |
| JP | 2019-182825 A | 10/2019 |
| JP | 2019-199469 A | 11/2019 |
| JP | 2020-138928 A | 9/2020 |
| JP | 2021-75531 A | 5/2021 |
| JP | 2022-157707 A | 10/2022 |
| WO | 96/25145 A1 | 8/1996 |
| WO | 2006/073786 A2 | 7/2004 |
| WO | 2005030205 A1 | 4/2005 |
| WO | 2006044155 A2 | 4/2006 |
| WO | 2007092620 A2 | 8/2007 |
| WO | 2018104950 A1 | 6/2018 |
| WO | 2018114557 A1 | 6/2018 |
| WO | 2018212846 A1 | 11/2018 |
| WO | 2019/060696 A1 | 3/2019 |
| WO | 2017040099 A1 | 3/2019 |
| WO | 2019/216381 A1 | 11/2019 |
| WO | 2020/106337 A1 | 5/2020 |
| WO | 2020/139525 A1 | 7/2020 |
| WO | 2022076398 | 4/2022 |
| WO | 2023/141334 A2 | 7/2023 |

OTHER PUBLICATIONS

Vickers et al., "The Future of Dry Eye Treatment: A Glance into the Therapeutic Pipeline", Ophthalmol Ther (2015) 4:69-78.

Matossian et al., Dry Eye Treatment with Topical Cyclosporine 0.1% in Chondroitin Sulfate Opthalmic Emulsion, Clinical Opthalmology (2021)15:1979-1984.

Mueller et al., "Refractive Surgery Alliance Issues Updated Nomenclature Recommendations", Opthalmology Advisor Opinion, https://www.ophthalmologyadvisor.com/topics/practice-management/refractive-surgery-alliance-offers-terminology-update/#:~:text=The%20adoption%20of%20the%20term,appropriate%20for%20their%20specific%20cases, accessed Oct. 18, 2023, published Jul. 10, 2023.

PCT/US2022/027177 International Search Report and Written Opinion mailed Jul. 25, 2022.

Limberg et al., "Topical Application of Hyaluronic Acid and Chondroitin Sulfate in the Treatment of Dry Eyes", American Journal of Ophthalmology, (1987)103(2):194-197.

* cited by examiner

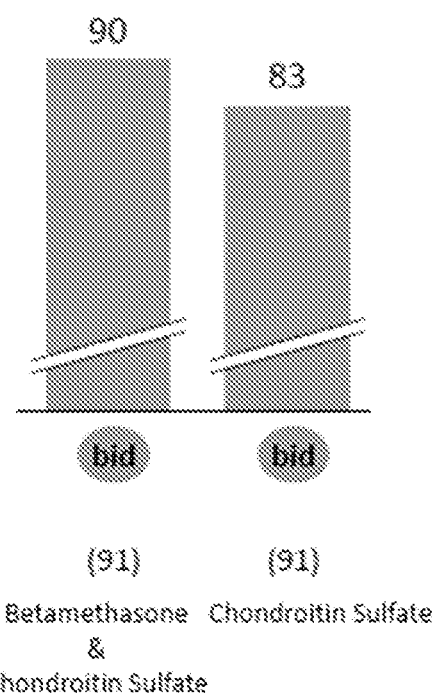

USE OF CHONDROITIN SULFATE FOR RELIEVING OCULAR PAIN

CROSS REFERENCE TO RELATED APPLICATIONS

This is a US national phase application under 35 USC §371 of international patent application no. PCT/US2022/027177, May 1, 2022, which itself claims benefit of priority to U.S. provisional patent application No. 63/186,747, filed May 10, 2021; the content of which is herein incorporated by reference in its entirety.

TECHNICAL FIELD

The invention relates to the use of chondroitin sulfate for the prevention and/or treatment of ocular pain or discomfort, such as occurring from ocular surgery and/or ocular surface disease.

BACKGROUND OF THE INVENTION

Eye pain is generally characterized into two different categories: ocular pain, which occurs on the eye's surface; and orbital pain, which occurs within the eye. Ocular pain can be caused by conjunctivitis, irritation from contact lenses, corneal abrasion, burns, blepharitis, stye, and dry eye disease.

Dry eye disease is frequently caused by decreased tear production. Decreased tear production can occur as a result of age, hormonal changes, various autoimmune diseases, and other factors, and may also be a side effect of certain medications, such as beta-blockers, antidepressants, antihistamines, etc. Dry eye disease can also occur after ocular surgery. Manipulation and contact between instruments, medications, surgical tools and the cornea can cause microscopic damage to the eye, thereby resulting in dry eye disease. This can negatively affect visual recovery and outcomes. That is, a healthy smooth cornea will tend to heal faster than a dry cornea with epithelial surface irregularities and tear film issues. Moreover, ocular surgery induced dry eye disease can be even more severe when the patient is older, as is often the case with cataract surgery.

Conventionally, ocular pain is treated with artificial tears. In more severe cases, eye drops incorporating a corticosteroid may be used. However, adverse and undesirable effects are commonly associated with steroid eye drops; and therefore, they are typically used sparingly. Among these effects include stinging, burning, itching or irritation of the eye, temporary cloudy vision, increased sensitivity to light, blurry vision, and allergic reactions.

Therefore, there remains a need for new therapeutic treatments to relieve ocular pain.

BRIEF SUMMARY OF THE INVENTION

The invention is directed to the use of chondroitin sulfate for the treatment of ocular pain or discomfort. An exemplary method of treating ocular pain or discomfort includes administering to an eye of a subject suffering from or at risk of suffering from ocular pain or discomfort, a therapeutically effective amount of chondroitin sulfate.

In some embodiments, the ocular pain or discomfort results from receiving a medical treatment, such as ocular surgery. Chondroitin sulfate is demonstrated herein to be surprisingly effective at reducing ocular pain or discomfort after undergoing ocular surgery. Accordingly, this disclosure describes uses of chondroitin sulfate for treating ocular pain or discomfort after receiving a medical treatment, which includes administering to an eye of a subject that has received a medical treatment that is likely to cause ocular pain or discomfort, a therapeutically effective amount of chondroitin sulfate. Such medical treatments can include various ocular surgeries, such as but not limited to cataract surgery.

Chondroitin sulfate can also be used to treat ocular pain or discomfort associated with a medical condition. Exemplary medical conditions include but are not limited to dry eye disease, contact lens induced ocular surface dry eye disease, preservative induced ocular surface disease, conjunctivitis, irritation from contact lenses, corneal abrasion, burns, blepharitis and stye. Such uses include administering a therapeutically effective amount of chondroitin sulfate to the subject's eye that is suffering from the ocular pain or discomfort resulting from a medical condition.

In each of the embodiments, the chondroitin sulfate is preferably administered topically to the eye. The chondroitin sulfate can be administered over any time sufficient to reduce ocular pain or discomfort. In instances of ocular surgery, the chondroitin sulfate can be administered over at least 7 days, optionally for 14 days or more after ocular surgery as a postop treatment regimen. In instances of disease, chondroitin sulfate can be administered whenever the subject feels pain or discomfort.

The chondroitin sulfate is preferably combined with a pharmaceutically acceptable carrier to form a pharmaceutical composition. Chondroitin sulfate can be at any suitable concentration but a range between 0.1% to 1.0% is typically preferred with a more preferred concentration of 0.25%. Chondroitin can be derived from shark, bovine or other source. In some embodiments, the chondroitin sulfate forms part of a pharmaceutical composition that consists essentially of chondroitin sulfate and a pharmaceutically acceptable carrier. In some embodiments, chondroitin sulfate forms part of a pharmaceutical composition that is free of corticosteroids. That is, the chondroitin sulfate-based pharmaceutical composition can be a steroid-free composition. However, in other embodiments, the pharmaceutical composition includes a therapeutically effective amount of chondroitin sulfate and a corticosteroid or other medication. In still further embodiments, the pharmaceutical composition includes chondroitin sulfate and betamethasone sodium phosphate.

In a related aspect, a method of treating an ocular surface disease is provided, which includes administering to a subject that suffers from an ocular surface disease a therapeutically effective amount of chondroitin sulfate. Nonlimiting examples of ocular surface diseases that can be treated include dry eye disease, contact lens induced ocular surface dry eye disease, and preservative induced ocular surface disease.

In another related aspect, a composition for the treatment of ocular pain or discomfort is provided, the composition consisting essentially of chondroitin sulfate and a pharmaceutically acceptable carrier. Such compositions are steroid-free.

BRIEF DESCRIPTION OF THE DRAWINGS

FIG. 1 is a chart demonstrating percent pain clearance two weeks after cataract surgery, where the subjects received a topical pharmaceutical formulation of either a combination of betamethasone sodium phosphate and chondroitin sulfate (left) or chondroitin sulfate (right).

DETAILED DESCRIPTION OF PREFERRED EMBODIMENTS

The invention demonstrates the use of chondroitin sulfate for the prevention and/or treatment of ocular pain or discomfort. It was surprisingly found that the administration of chondroitin sulfate as a sole active ingredient significantly reduced ocular pain associated with dry eye disease after undergoing ocular surgery. Pain was further reduced when provided in combination with a steroid.

Chondroitin sulfate is a chemical normally found in cartilage around joints in the body. Commercially, it is both manufactured from animal sources (e.g. cow cartilage) and produced chemically in the lab. Prior to cataract removal, chondroitin sulfate is typically injected into the eye to maintain a protective chamber during ocular surgery. While chondroitin sulfate is commonly used during surgical procedures, it is not conventionally prescribed during recovery. Nor is it used to treat ocular pain. This disclosure newly documents the benefits of using chondroitin sulfate as a treatment for ocular pain or discomfort, such as pain that commonly results from ocular surgery and/or for the prevention or reduction of pain or discomfort after ocular surgery. This disclosure also newly documents the benefits of using chondroitin sulfate to treat pain or discomfort resulting from dry eye disease generally and in particular ocular surgery induced dry eye disease, contact lens induced ocular surface dry eye disease, preservative induced ocular surface disease, and other ocular surface diseases that cause pain or discomfort.

To assess the safety, tolerability and efficacy of various solutions for treating ocular surgery induced dry eye disease, a multicenter, randomized, double-masked, parallel group study was conducted. In particular, the study included approximately 182 subjects that underwent uncomplicated unilateral cataract surgery (phacoemulsification or extracapsular extraction; surgery without aid of a femto laser). The subjects were treated with either a pharmaceutical composition of betamethasone sodium phosphate and chondroitin sulfate or a pharmaceutical composition of chondroitin sulfate. In particular, one drop of study drug was self-instilled by the subject (or instilled by the subject's caregiver) BID as directed (once in the morning and once in the evening, preferably 8-12 hours apart) in the surgery eye (study eye) for 16 days: the day prior to cataract surgery, the day of cataract surgery (at least one hour prior to surgery and then once in the evening following surgery), and continued BID postoperatively for 14 days.

The betamethasone/chondroitin sulfate pharmaceutical composition contained betamethasone sodium phosphate (0.2% betamethasone sodium phosphate) sodium thiosulfate, sodium chondroitin sulfate, Dextran-70, edetate disodium, poloxamer 407, glycerin, potassium chloride, sodium phosphate dibasic anhydrous, sodium phosphate monobasic anhydrous, sodium hydroxide, hydrochloric acid, and sterile water for injection. The formulation was sterile and non-preserved.

The chondroitin sulfate pharmaceutical composition contained sodium thiosulfate, sodium chondroitin sulfate, Dextran-70, edetate disodium, poloxamer 407, glycerin, potassium chloride, sodium phosphate dibasic anhydrous, sodium phosphate monobasic anhydrous, sodium hydroxide, hydrochloric acid, and sterile water for injection. The formulation was sterile and non-preserved.

Primary efficacy analysis was conducted using a last-observation-carried-forward (LOCF) method. The primary efficacy endpoint is the proportion of subjects with an ACC grade of 0 at Day 15. Anterior chamber cells were counted and graded according to TABLE 1.

TABLE 1

| Grading and Counting of Anterior Chamber Cells | |
|---|---|
| Grade | Cell Count |
| 0 | 0 |
| 1 | 1-10 |
| 2 | 11-20 |
| 3 | 21-50 |
| 4 | >50 |

The secondary efficacy endpoint is the proportion of subjects who achieve a pain score of 0 on the VAS (0 to 100 mm scale) at each post-surgical assessment. Differences in proportions between the active treatment (with 0.2% betamethasone sodium phosphate) and placebo (without steroid) were calculated for each time point, with a 95% confidence interval for the differences. The secondary efficacy analysis is the proportion of subjects in each treatment group with an ACF grade of 0 at each study visit.

FIG. 1 is a chart of percent pain clearance at 2 weeks post-surgery. It was found that while the combined betamethasone/chondroitin sulfate composition was more efficacious than the chondroitin sulfate composition alone; the chondroitin sulfate composition, which is a steroid-free formulation performed surprisingly well. The combined betamethasone/chondroitin sulfate treatment demonstrated 90% pain clearance and the chondroitin sulfate treatment demonstrated 83% pain clearance. This supports at least two specific uses for chondroitin sulfate. On the one hand, chondroitin sulfate can be combined with a corticosteroid in a pharmaceutical composition to provide a highly effective treatment against ocular pain, and on the other hand, chondroitin sulfate can also be provided in a steroid-free pharmaceutical composition for the treatment of ocular pain or discomfort.

One having ordinary skill in the art which the invention belongs would appreciate that the above demonstrates new and surprising therapeutic uses for chondroitin sulfate. In particular, chondroitin sulfate was highly efficacious at clearing ocular pain (83%) and therefore provides a steroid-free alternative for treating postop induced ocular pain or discomfort. Moreover, the steroid-free use of chondroitin sulfate will have fewer adverse treatment effects than conventional steroid treatments. As such, chondroitin sulfate itself can be used as an active ingredient for the treatment, prevention or amelioration of ocular pain or discomfort caused by medical procedures or disease.

A such, an exemplary method for treating ocular pain or discomfort after receiving a medical treatment can include administering to an eye of a patient that has received a medical treatment that is likely to cause ocular pain, a therapeutically effective amount of chondroitin sulfate. Likewise, an exemplary method of treating ocular pain or discomfort can include administering to an eye of a subject suffering from a medical condition that results in ocular pain or discomfort, a therapeutically effective amount of chondroitin sulfate.

By "therapeutically effective amount" it is meant that the amount of active ingredient or pharmaceutical composition administered is effective to prevent, alleviate, or ameliorate one or more symptoms associated with a medical condition. Examples of symptoms that can be prevented, reduced or ameliorated using pharmaceutical compositions that contain, at least in part, chondroitin sulfate, include pain; inflammation; stinging, burning or scratchy sensation in the eyes; stringy mucus in or around the eyes; sensitivity to light; eye redness; sensation of having something in the eyes; difficulty wearing contact lenses; difficulty with nighttime driving; watery eyes; blurred vision and eye fatigue. It is envisioned that a therapeutically effective amount may vary depending on the disorder or condition and its severity, the age, weight, etc. of the subject to be treated. A therapeutically effective amount can be provided all at once in a single administration or can be fractional amounts that provide the effect in several administrations. The precise determination of what would be considered therapeutically effective may be based on factors individual to each subject, including their size, age, injury and or severity of disease being treated and amount of time since the injury occurred or the disease began. As general guidance one or a few drops of a 0.1% to 1.0% eye drop solution of chondroitin sulfate should be effective for most uses, and a 0.25% solution formulated as eye drops tends to be most preferred. One having ordinary skill in the art to which the invention belongs will be able to determine the therapeutically effective amount based on these conditions which are routine in the art.

In view of the above, in some embodiments the pharmaceutical composition consists essentially of chondroitin sulfate and a pharmaceutically acceptable carrier. For completeness, by "pharmaceutical composition" it is meant that the active ingredient is combined with a pharmaceutically acceptable carrier, such as a diluent or excipient, that is compatible with the active ingredient and any other ingredients forming the pharmaceutical composition and is suitable for the intended route of administration. A nonlimiting example is the formulation of eye drops for topical administration having chondroitin sulfate at a concentration of 0.1% to 1.0% or at a concentration of 0.25%. By "consisting essentially of" it is meant that the pharmaceutical composition lacks further active ingredients that materially affect the treatment, prevention or amelioration of symptoms associated with condition to be treated, namely, ocular pain or discomfort. That is, while chondroitin sulfate can be used with a corticosteroid, it can also be used without a corticosteroid due to its efficacy of clearing pain associated with ocular surface disease or injury. Reagents such as those commonly associated with the preparation of pharmaceuticals, such as excipients, diluents and lubricants are not excluded by the term "consisting essentially of" as they do not themselves materially treat the underlying medical condition or symptom.

An exemplary pharmaceutical composition that is steroid-free and/or "consists essentially of" chondroitin sulfate includes a combination of sodium thiosulfate, sodium chondroitin sulfate, Dextran-70, edetate disodium, poloxamer 407, glycerin, potassium chloride, sodium phosphate dibasic anhydrous, sodium phosphate monobasic anhydrous, sodium hydroxide, hydrochloric acid, and sterile water.

Chondroitin sulfate may also be used to treat contact lens discomfort or contact lens induced ocular surface dry eye disease. Contact lens discomfort is often associated with dry eyes. A contact lens divides the tear film into two layers: the pre and post-lens tear film. Bifurcating the film into two layers increases friction between the contact lens and ocular surface, which can cause dry eye disease. Accordingly, also provided is a method of treating an ocular surface disease, which includes administering to an eye of a subject suffering from an ocular surface disease, a therapeutically effective amount of chondroitin sulfate. In furtherance of this, in some embodiments ocular surface disease is a dry eye disease, such as contact lens induced ocular surface dry eye disease.

Chondroitin sulfate can also be used to treat other ocular surface diseases. For example, glaucoma medications can be associated with toxicities to the ocular surface. Common therapies for glaucoma treatment include the use of prostaglandin analogs, beta-adrenergic antagonists, alpha-adrenergic agonists, and carbonic anhydrase inhibitors. Due to either the added preservative or the active ingredient of the medication itself, these topical treatments for glaucoma can cause or worsen ocular surface disease. Moreover, preservatives such as benzalkonium chlorides have widespread applications, including use in eye drops. Such preservatives can cause dry eye disease. Accordingly, chondroitin sulfate can be used to treat ocular surface disease induced by preservatives or other active ingredients, such as those used in the treatment of glaucoma. As such methods for treating ocular surface disease can include administering to an eye of a subject suffering from preservative induced ocular surface disease, a therapeutically effective amount of chondroitin sulfate; and another exemplary embodiment includes administering to an eye of a subject suffering from glaucoma, a therapeutically effective amount of a glaucoma therapeutic and chondroitin sulfate.

Though nonlimiting, this disclosure documents that administration of chondroitin sulfate twice daily (BID) for two weeks, from the day of receiving cataract surgery, cleared 83% of ocular pain. As such, administration of chondroitin sulfate for less than two weeks after receiving ocular surgery will also clear pain; however, pain clearance might be below 83% in some subjects. Accordingly, within the scope of the disclosure, chondroitin sulfate is preferably administered for at least 1 day, 2 days, 3 days, 4 days, 5 days, 6 days, 7 days, 8 days, 9 days, 10 days, 11 days, 13 days, 14 days or more. However, in other instances chondroitin sulfate can be administered when the subject feels pain or discomfort. The artisan will also appreciate that while chondroitin sulfate is preferably administered topically via eye drops twice daily (BID), it can also be administered once daily, three times daily (TID), four times daily (QID) or more.

While chondroitin sulfate has been found highly efficacious at treating ocular pain, in some instances it may be beneficial to combine the chondroitin sulfate with a steroid, especially in instances of significant inflammation. For example, significant inflammation may occur after ocular surgery and thus a subject that has undergone ocular surgery may be provided postop with a pharmaceutical composition including chondroitin sulfate and a corticosteroid, preferably betamethasone sodium phosphate (e.g. 0.2% betamethasone sodium phosphate). In such compositions, the active ingredients (e.g. chondroitin sulfate and betamethasone sodium phosphate) are providing in a therapeutically effective amount. In furtherance of the above, the chondroitin sulfate was also administered with the corticosteroid betamethasone sodium phosphate during clinical testing. This combined betamethasone/chondroitin sulfate composition was administered twice daily (BID) for two weeks, from the day of receiving cataract surgery. The combined betamethasone/chondroitin sulfate composition cleared 90% of pain and 56% of inflammation. As such, the addition of a corticosteroid, preferably betamethasone sodium phosphate, is also encompassed by the methods and compositions described within this document.

For completeness, administration of chondroitin sulfate and a corticosteroid is preferably accomplished by way of administering a pharmaceutical composition that itself contains both chondroitin sulfate and the corticosteroid; however, it is also envisioned that one pharmaceutical composition that contains chondroitin sulfate in a steroid-free formulation and another pharmaceutical composition that contains a corticosteroid in a chondroitin sulfate-free formulation can be provided separately then administered at about a same time. Though nonlimiting, an exemplary treatment regimen can include administering chondroitin sulfate and the corticosteroid for at least 1 day, 2 days, 3 days, 4 days, 5 days, 6 days, 7 days, 8 days, 9 days, 10 days, 11 days, 13 days, 14 days or more. The artisan will also appreciate that while the composition(s) is preferably administered topically via eye drops twice daily (BID), it can also be administered once daily, three times daily (TID), four times daily (QID) or more.

In still further treatments regimens, the subject is provided with both a steroid-free chondroitin sulfate pharmaceutical composition and a pharmaceutical composition that includes the steroid. This approach may be preferred in instances where the pharmaceutical composition that includes the steroid is to be used sparingly, such as in instances of severe inflammation or discomfort, while the pharmaceutical composition that is steroid-free is used more regularly for pain maintenance.

Example 1

Preparing Pharmaceutical Composition No. 1

Pharmaceutical compositions were prepared as described below. The following products were used in the amounts specified in TABLE 2:

TABLE 2

Pharmaceutical Composition No. 1

| Amount | Product |
|---|---|
| 0.25 g | chondroitin sulfate (bovine) |
| 0.25 g | powdered dextran-70 |
| 0.1 g | edetate disodium powder |
| 0.03 g | potassium chloride |
| 0.20 g | PLURONIC ® F-127 |
| 0.2 g | glycerol |
| 0.9 g | sodium phosphate dibasic anhydrous |
| 0.18 g | sodium phosphate monobasic anhydrous |
| 100 mL | sterile injectable water |

Chondroitin sulfate, dextran, potassium phosphate, dibasic and monobasic sodium phosphate, potassium chloride, EDTA, and PLURONIC® F-127 were combined with about 90% of water and stirred until completely dissolved followed by adding glycerol with continued stirring. The pH of the solution was then adjusted to about 7.0-7.4 using sodium hydroxide solution. The solution was then filtered through a 0.2 micron filter into a sterile droptainer and sealed.

Example 2

Preparing Pharmaceutical Composition No. 2

Pharmaceutical compositions were prepared as described below. The following products were used in the amounts specified in TABLE 3:

TABLE 3

Pharmaceutical Composition No. 2

| Amount | Product |
|---|---|
| 0.50 g | chondroitin sulfate (bovine) |
| 0.25 g | powdered dextran-70 |
| 0.1 g | edetate disodium powder |
| 0.03 g | potassium chloride |
| 0.20 g | PLURONIC ® F-127 |
| 0.2 g | Glycerol |
| 0.9 g | sodium phosphate dibasic anhydrous |
| 0.18 g | sodium phosphate monobasic anhydrous |
| 100 mL | sterile injectable water |

Example 3

Preparing Pharmaceutical Composition Nos. 3 and 4

A pharmaceutical composition was prepared as described below. The following products were used in the amounts specified in TABLE 4:

TABLE 4

Preparation of Pharmaceutical Composition Nos. 3 and 4

| Amount | Product |
|---|---|
| 0.02 or 0.04 g | betamethasone sodium phosphate |
| 0.25 g | chondroitin sulfate (bovine) |
| 0.25 g | powdered dextran-70 |
| 0.1 g | edetate disodium powder |
| 0.30 g | powdered sodium thiosulfate pentahydrate |
| 0.03 g | potassium chloride |
| 0.20 g | PLURONIC ® F-127 |
| 0.2 g | glycerol |
| 0.9 g | sodium phosphate dibasic anhydrous |
| 0.18 g | sodium phosphate monobasic anhydrous |
| 100 mL | sterile injectable water |

Chondroitin sulfate, dextran, sodium thiosulfate, phosphate buffer, potassium chloride, EDTA, and PLURONIC® F-127 were combined with about 90% of the water and stirred until completely dissolved followed by addition of glycerol with continued stirring. The pH of the solution was then adjusted to about 7.0 using sodium hydroxide. A stock solution of 1% betamethasone sodium phosphate was prepared by dissolving 1 gm of betamethasone sodium phosphate powder in 100 mL water and confirming the stock solution concentration by HPLC. Then 2 (Composition 3) or 4 ml (Composition 4) of the 1% betamethasone sodium phosphate stock solution was then added to the mixture with continued stirring. The solution was then filtered through a 0.2 micron filter into sterile dropper bottles or unit dose vials.

Example 4

Preparing Pharmaceutical Composition No. 5

A pharmaceutical composition was prepared as described below. The following products were used in the amounts specified in TABLE 5:

TABLE 5

Preparation of Pharmaceutical Composition No. 5

| Amount | Product |
|---|---|
| 0.2 g | betamethasone sodium phosphate |
| 0.25 g | chondroitin sulfate (bovine) |
| 0.25 g | powdered dextran-70 |
| 0.1 g | edetate disodium powder |
| 0.30 g | powdered sodium thiosulfate pentahydrate |
| 0.015 g | potassium chloride |
| 0.20 g | PLURONIC ® F-127 |
| 0.2 g | Glycerol |
| 0.95 g | sodium phosphate dibasic anhydrous |
| 0.2 g | sodium phosphate monobasic anhydrous |
| 0.20 g | Hypromellose |
| 0.006 g | Magnesium chloride hexahydrate |
| 0.0096 g | Calcium Chloride Dihydrate |
| 100 mL | sterile injectable water |

Chondroitin sulfate, dextran, sodium thiosulfate, phosphate buffer, potassium chloride, EDTA, magnesium chloride. calcium chloride, hypromellose, and PLURONIC® F-127 were combined with about 90% of the water and stirred until completely dissolved followed by addition of glycerol with continued stirring. The pH of the solution was then adjusted to about 7.0 using sodium hydroxide. A stock solution of 1% betamethasone sodium phosphate was prepared by dissolving 1 gm of betamethasone sodium phosphate powder in 100 mL water and confirming the stock solution concentration by HPLC. Then 20 ml of the 1% betamethasone sodium phosphate stock solution was then added to the mixture with continued stirring. The solution was then filtered through a 0.2 micron filter into sterile dropper bottles or unit dose vials.

Example 5

Preparing Pharmaceutical Composition No. 6

A pharmaceutical composition was prepared as described below. The following products were used in the amounts specified in TABLE 6:

TABLE 6

Preparation of Pharmaceutical Composition No. 6

| Amount | Product |
|---|---|
| 0.25 g | chondroitin sulfate (bovine) |
| 0.25 g | powdered dextran-70 |
| 0.1 g | edetate disodium powder |
| 0.30 g | powdered sodium thiosulfate pentahydrate |
| 0.015 g | potassium chloride |
| 0.20 g | PLURONIC ® F-127 |
| 0.2 g | Glycerol |
| 0.95 g | sodium phosphate dibasic anhydrous |
| 0.2 g | sodium phosphate monobasic anhydrous |
| 0.20 g | Hypromellose |
| 0.006 g | Magnesium chloride hexahydrate |
| 0.0096 g | Calcium Chloride Dihydrate |
| 100 mL | sterile injectable water |

Chondroitin sulfate, dextran, sodium thiosulfate, phosphate buffer, potassium chloride, EDTA, magnesium chloride. calcium chloride, hypromellose, and PLURONIC® F-127 were combined with about 90% of the water and stirred until completely dissolved followed by addition of glycerol with continued stirring. The pH of the solution was then adjusted to about 7.0 using sodium hydroxide. The solution was then filtered through a 0.2 micron filter into sterile dropper bottles or unit dose vials.

Although the invention has been described with the reference to the above examples, it will be understood that modifications and variations are encompassed within the spirit and scope of the invention. Accordingly, the invention is limited only by the finally granted claims.

What is claimed is:

1. A method of treating ocular pain or discomfort after ocular surgery, the method comprising: topically administering eye drops to an eye of a subject that has undergone ocular surgery, a therapeutically effective amount of a composition consisting essentially of 0.1% to 1.0% wt/wt chondroitin sulfate and a lubricant in a pharmaceutically acceptable carrier.

2. The method of claim 1, wherein the ocular surgery is cataract surgery.

3. The method of claim 1, wherein the composition is administered over at least 7 days, optionally for 14 days or more.

4. The method of claim 1, wherein the lubricant comprises Dextran-70 and glycerol.

5. A method of treating ocular pain or discomfort after ocular surgery, the method comprising: topically administering eye drops to an eye of a subject that has undergone ocular surgery, a composition comprising 0.1% to 1.0% wt/wt chondroitin sulfate in a pharmaceutically acceptable carrier.

6. The method of claim 5, wherein the composition is free of corticosteroids.

7. The method of claim 5, wherein the composition is administered for at least 7 days.

8. The method of claim 5, wherein the composition further comprises a lubricant in the pharmaceutically acceptable carrier.

9. The method of claim 8, wherein the lubricant comprises Dextran-70 and glycerol.

10. The method of claim 5, wherein the ocular surgery is cataract surgery.

\* \* \* \* \*